United States Patent
Oikawa

(10) Patent No.: US 8,494,118 B2
(45) Date of Patent: Jul. 23, 2013

(54) RADIOGRAPHIC APPARATUS

(75) Inventor: Shiro Oikawa, Otsu (JP)

(73) Assignee: Shimadzu Corporation, Kyoto (JP)

( * ) Notice: Subject to any disclaimer, the term of this patent is extended or adjusted under 35 U.S.C. 154(b) by 340 days.

(21) Appl. No.: 13/027,386

(22) Filed: Feb. 15, 2011

(65) Prior Publication Data

US 2011/0200169 A1     Aug. 18, 2011

(30) Foreign Application Priority Data

Feb. 18, 2010  (JP) ................................. 2010-033425

(51) Int. Cl.
*H05G 1/64*         (2006.01)

(52) U.S. Cl.
USPC .......... 378/98.12; 378/62; 378/98.8; 378/207

(58) Field of Classification Search
USPC ........................ 378/62, 98.8, 98.12, 154, 207
See application file for complete search history.

(56) References Cited

U.S. PATENT DOCUMENTS

| | | | | |
|---|---|---|---|---|
| 5,050,198 | A * | 9/1991 | Honda | 378/98.2 |
| 6,480,574 | B2 | 11/2002 | Goto | |
| 6,542,575 | B1 * | 4/2003 | Schubert et al. | 378/98.4 |
| 6,850,597 | B2 * | 2/2005 | Matsumoto et al. | 378/154 |
| 7,039,151 | B2 * | 5/2006 | Tsujii | 378/7 |
| 8,284,902 | B2 * | 10/2012 | Fujita | 378/155 |
| 2001/0033638 | A1 * | 10/2001 | Inoue | 378/154 |
| 2011/0110500 | A1 * | 5/2011 | Fujita | 378/154 |
| 2011/0200169 | A1 * | 8/2011 | Oikawa | 378/42 |

FOREIGN PATENT DOCUMENTS

JP      2002-336220 A      11/2002

OTHER PUBLICATIONS

The First Office Action for the Application No. 201010621681.5 from The State Intellectual Property Office of the People's Republic of China dated Apr. 12, 2012.

* cited by examiner

*Primary Examiner* — Thomas R Artman
(74) *Attorney, Agent, or Firm* — Cheng Law Group, PLLC

(57) ABSTRACT

A radiographic apparatus includes a radiation source for emitting radiation, a radiation detecting device for detecting the radiation, a radiation grid placed to cover a radiation detecting plane of the radiation detecting device, a pattern storage device for storing a plurality of patterns of shadows of the radiation grid falling on the radiation detecting device, an image generating device for generating an original image showing the object under examination and the shadows of the radiation grid, based on detection signals outputted from the radiation detecting device, a grid shadow estimating device for estimating a pattern of superimposed grid shadows, which are the shadows of the radiation grid appearing on the original image, from the patterns of shadows stored in the pattern storage device, and a removing device for removing the shadows of the radiation grid from the original image based on the superimposed grid shadows estimated.

10 Claims, 10 Drawing Sheets

Fig.17
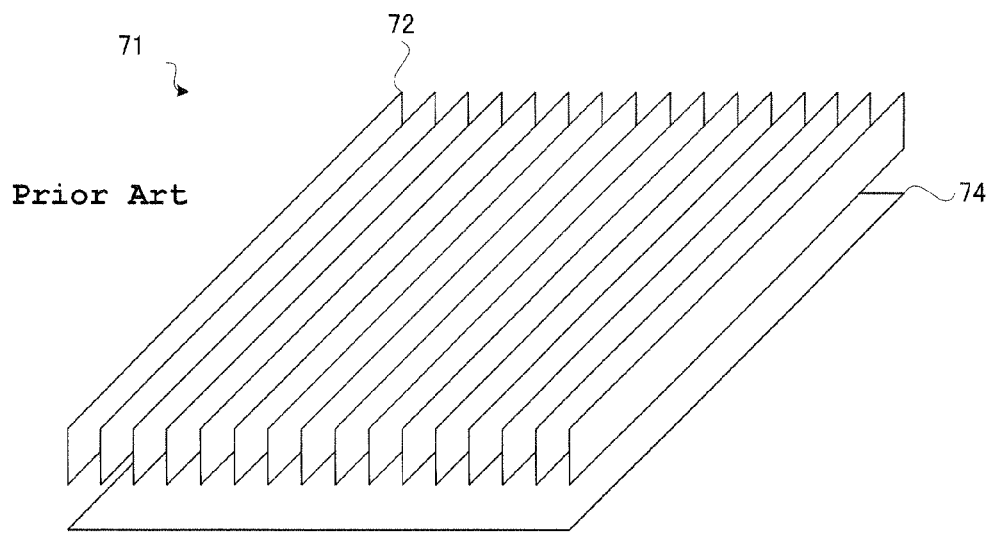
Prior Art
Fig.18A
Prior Art
Fig.18B
Prior Art
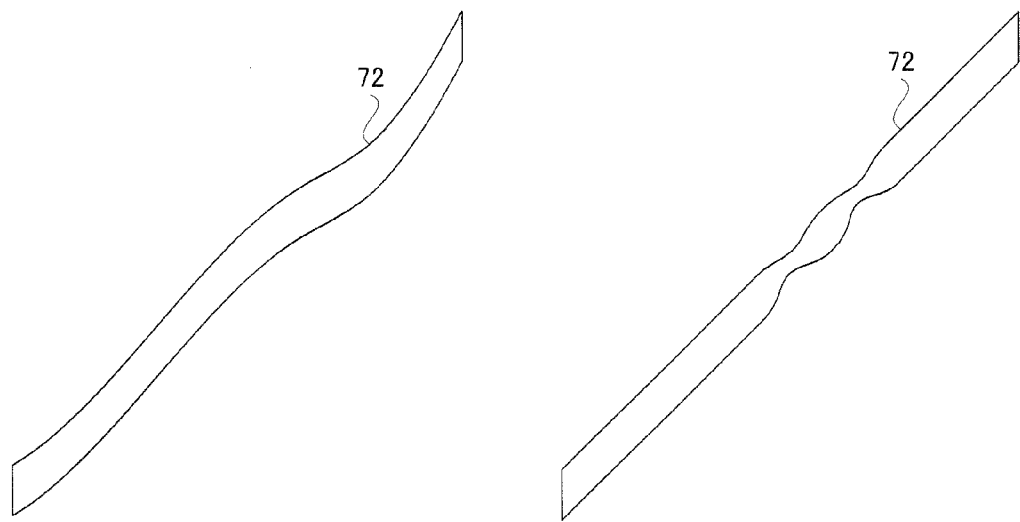

RADIOGRAPHIC APPARATUS

BACKGROUND OF THE INVENTION (1) Field of the Invention

This invention relates to a radiographic apparatus including a radiation source and a radiation detector. More particularly, the invention relates to a radiographic apparatus including a radiation source and a radiation detector which are both movable, the radiation detector having a radiation grid attached thereto.

(2) Description of the Related Art

Among radiographic apparatus for acquiring fluoroscopic images of objects under examination or patients, there is one constructed to emit cone-shaped radiation beams from a radiation source toward a patient, and detect with a flat panel detector (hereinafter abbreviated as FPD) radiation transmitted through the patient. Such a construction is shown in Cited Document 1. The radiation, when transmitted through the patient, becomes scattered inside the patient, resulting in scattered radiation incident on the FPD to affect the fluoroscopic image. This becomes a factor for worsening the contrast of the fluoroscopic images. In order to prevent the scattered radiation from reaching the FPD, as shown in FIG. 17, a radiation grid 71 may be provided to cover the radiation detecting plane of the FPD. The radiation grid 71 is constructed to have absorbing foil strips 72 arranged in a predetermined direction.

Strictly speaking, these absorbing foil strips 72 will also absorb direct radiation. Therefore, shadows of the absorbing foil strips 72 will fall on the FPD 74. The luminosity of portions of the fluoroscopic image corresponding to the detecting elements reflecting these shadows will become lower than that of portions corresponding to the detecting elements free of the shadows. This results in striped false images appearing on the fluoroscopic image.

Such false images appearing on the fluoroscopic image are obstructive to diagnosis of a site of interest. In a known method of removing these false images, the shadows of the radiation grid 71 are once imaged and the false images are removed based on this. Such method projects the shadows of the radiation grid 71 onto the FPD 74 without a patient placed between the radiation source and FPD 74, and forms a pattern of the radiation grid shadows. When actually removing the false images, the pattern of the radiation grid shadows is first increased or decreased in size, moved and rotated. Then, the false images are removed by superimposing the pattern on the fluoroscopic image of the patient (see Japanese Unexamined Patent Publication No. 2002-336220, for example).

However, the conventional radiographic apparatus has the following drawback. The conventional practice of removing the false images due to the shadows of the radiation grid 71 is premised on that the absorbing foil strips 72 of the radiation grid 71 are perfectly linear. Actually, the absorbing foil strips 72 of the radiation grid 71 are bent to meander as shown in FIG. 18A, or are twisted as shown in FIG. 18B. Such bending or twisting is slight and does not seriously block passage of direct radiation, but is important in the process of removing the false images.

Variations in the direction of radiation irradiating the absorbing foil strips 72, if the latter are bent or twisted, will also vary the shapes of the shadows. That is, in the radiographic apparatus, the shapes of the shadows falling on the FPD will vary with variations in the positional relationship between the radiation source, radiation grid 71, and FPD. Then, the pattern of the false images will also change. According to the conventional construction, it is impossible to foresee variations in the pattern of the false images complicated by bending or twisting of the absorbing foil strips 72. Therefore, the false images superimposed on the fluoroscopic image cannot be removed sufficiently.

SUMMARY OF THE INVENTION

This invention has been made having regard to the state of the art, and its object is to provide a radiographic apparatus which can effectively remove false images due to shadows of a radiation grid and superimposed on a fluoroscopic image, thereby to acquire a fluoroscopic image suitable for diagnosis.

The above object is fulfilled, according to this invention, by a radiographic apparatus comprising a radiation source for emitting radiation; a radiation detecting device for detecting the radiation; a radiation grid placed to cover a radiation detecting plane of the radiation detecting device; a pattern storage device for storing a plurality of patterns of shadows of the radiation grid falling on the radiation detecting device; an image generating device for generating an original image showing the object under examination and the shadows of the radiation grid, based on detection signals outputted from the radiation detecting device; a grid shadow estimating device for estimating a pattern of superimposed grid shadows, which are the shadows of the radiation grid appearing on the original image, from the patterns of shadows stored in the pattern storage device; and a removing device for removing the shadows of the radiation grid from the original image based on the superimposed grid shadows estimated; wherein the grid shadow estimating device is arranged to estimate the superimposed grid shadows based on a positional relationship between the radiation source and the radiation detecting device occurring at a time of acquiring the original image.

The above radiographic apparatus can remove the superimposed grid shadows from the original image. It is difficult to foresee the shape of the superimposed grid shadows appearing on the original image. This is because the mechanical construction of the radiation grid does not conform to the setting. Moreover, the shape of the superimposed grid shadows appearing on the original image varies with the positional relationships between the radiation source and radiation detecting device, which makes it still more difficult to foresee the shape of the superimposed grid shadows appearing on the original image. This invention provides the grid shadow estimating device which estimates a pattern of the superimposed grid shadows from a plurality of patterns of the shadows stored in the pattern storage device, and the removing device which removes the shadows of the radiation grid from the original image based on the estimated shadows of the radiation grid appearing on the original image. The grid shadow estimating device estimates the superimposed grid shadows based on the positional relationship between the radiation source and radiation detecting device at the time of acquiring the original image. Therefore, this invention can remove the superimposed grid shadows from the original image.

It is preferred that the above radiation grid includes absorbing foil strips extending in a first direction and arranged in a second direction; the grid shadow estimating device is arranged to estimate the superimposed grid shadows based on the positional relationship between the radiation source and the radiation detecting device occurring at the time of acquiring the original image, which relationship includes (A) a shift range which is a range of variations in a distance between the radiation source and the radiation detecting device, and (B) a second direction shift amount which is an amount of shift in the second direction between the radiation source and the radiation detecting device; and the patterns of shadows of the radiation grid stored in the pattern storage device are obtained by serially acquiring radiological images while moving the radiation source at predetermined intervals in the second direction relative to the radiation detecting device, with the radiation grid covering the detecting plane of the radiation detecting device.

According to the above construction, the superimposed grid shadows are estimated using a distance (shift range Zf) between the radiation source and the radiation detecting device and a shift amount (second direction shift amount: transverse shift amount Xf) of the radiation source and the radiation detecting device in the direction of arrangement of the absorbing foil strips (in the second direction). When the radiation source moves toward or away from the radiation detecting device, or shifts in the second direction relative thereto, the shape of the superimposed grid shadows will change significantly. In view of such a situation, the above construction takes the second direction shift amount into consideration in estimating the shape of the superimposed grid shadows.

It is preferred that the above intervals for moving the radiation source when obtaining the patterns of shadows of the radiation grid are determined to include a radiation emitted from the radiation source toward one end in the second direction of the radiation detecting device when the radiation source and the radiation detecting device have a minimum distance therebetween at the time of acquiring the original image, and when the radiation source is shifted to a maximum extent toward the other end in the second direction; and a radiation emitted from the radiation source toward the other end in the second direction of the radiation detecting device when the radiation source and the radiation detecting device have the minimum distance therebetween at the time of acquiring the original image, and when the radiation source is shifted to a maximum extent toward the one end in the second direction.

According to the above construction, the range of movement of the radiation source at the time of radiographing the patterns of the shadows of the radiation grid is determined with reference to the state where the radiation source and radiation detecting device are the closest to each other when acquiring the original image of the object under examination. In this state, as seen from the radiation detecting device, an apparent moving range in the second direction of the radiation source becomes the most intense. According to the above construction, even when the radiation source and radiation detecting device are the closest to each other, a pattern of the shadows of the radiation grid can be acquired reliably. Consequently, the pattern storage device can exhaustively store data about possible shapes of the superimposed grid shadows.

It is also preferred that the patterns of shadows of the radiation grid stored in the pattern storage device are compressed in the first direction.

The above construction can reduce the storage capacity of the pattern storage device.

It is also preferred that the radiation grid includes shielding members attached thereto and having grooves extending in the first direction, the second direction being a longitudinal direction, and the first direction being a transverse direction, the apparatus further comprising a shift amount calculating device for calculating the second direction shift amount at the time of acquiring the original image, based on shadows of the shielding members appearing on the original image.

The above construction clarifies a specific way to calculate the second direction shift amount. That is, the radiation grid has, attached thereto, the shielding members having grooves extending in the first direction. The second direction shift amount at the time of acquiring the original image is calculated based on the shadows of the shielding members appearing on the original image. Consequently, the second direction shift amount is calculated reliably.

It is further preferred that the shielding members are provided as a pair which are arranged at opposite ends in the first direction of the radiation grid.

The above construction shows a specific arrangement of the shielding members. With the pair of shielding members provided at the opposite ends in the first direction of the radiation grid, the second direction shift amount can be calculated for two locations on the radiation grid. Thus, the second direction shift amount is calculated reliably.

It is also preferred that the patterns of shadows of the radiation grid stored in the pattern storage device are radiological images; the radiological images having, related therewith, position information on the radiation source relative to the radiation detecting device at times the radiological images are acquired; and the grid shadow estimating device is arranged to estimate the pattern of the superimposed grid shadows while referring to the position information related with the radiological images.

The above construction gives a specific example of the patterns of shadows of the radiation grid. That is, the patterns of shadows of the radiation grid are radiological images which have, related thereto, position information on the radiation source relative to the radiation detecting device at times the radiological images are acquired. The position information related with the radiological images is referred to when estimating the pattern of the superimposed grid shadows.

It is further preferred that the grid shadow estimating device is arranged to estimate the pattern of the superimposed grid shadows by linearly interpolating the radiological images in the second direction.

The above construction gives a specific example of the way to estimate the pattern of the superimposed grid shadows. By estimating the pattern of the superimposed grid shadows using linear interpolation, the superimposed grid shadows can be estimated more simply.

It is also preferred that the grid shadow estimating device is arranged, in advance of original image radiography, to calculate and acquire the patterns of shadows of the radiation grid discretely while virtually changing the positional relationship between the radiation source and the radiation detecting device; and the removing device is arranged to remove the shadows of the radiation grid from the original image using a pattern of shadows of the radiation grid acquired from a positional relationship nearest to the positional relationship at the time of original image radiography.

The above construction is suitable where original image radiography is carried out a plurality of times with high frequency, such as dynamic image radiography or tomography. That is, the patterns of shadows of the radiation grid are acquired beforehand by the grid shadow estimating device, and there is no need to estimate a pattern of shadows of the radiation grid when the original image is acquired. The removing device removes the shadows of the radiation grid from the original image using the pattern of shadows of the radiation grid acquired from a positional relationship nearest to the positional relationship between the radiation source and the radiation detecting device at the time of original image radiography. Thus, when the radiography is completed, the pattern of superposed grid shadows can be removed promptly.

It is further preferred that the above grid shadow estimating device is arranged, based on a shift range set in advance of original image radiography, to calculate and acquire the patterns of shadows of the radiation grid discretely while virtually changing the second direction shift amount between the radiation source and the radiation detecting device; and the removing device is arranged to remove the shadows of the radiation grid from the original image using a pattern of shadows of the radiation grid acquired from a positional relationship nearest to the positional relationship at the time of original image radiography.

The above construction is still more suitable where original image radiography is carried out a plurality of times with high frequency, such as dynamic image radiography or tomography. That is, based on a distance between the radiation source and radiation detecting device, the grid shadow estimating device calculates and acquires patterns of shadows of the radiation grid discretely while virtually changing the second direction shift amount between the radiation source and radiation detecting device. This can simplify operation of the grid shadow estimating device.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 17 is a view illustrating a conventional construction;

FIG. 18A is a view illustrating a conventional construction; and

FIG. 18B is a view illustrating a conventional construction.

DESCRIPTION OF THE PREFERRED EMBODIMENTS

A radiographic apparatus according to this invention will be described hereinafter with reference to the drawings. X-rays in Embodiment 1 are one example of radiation according to this invention.

Embodiment 1

<Construction of X-Ray Apparatus>

Figure 1:
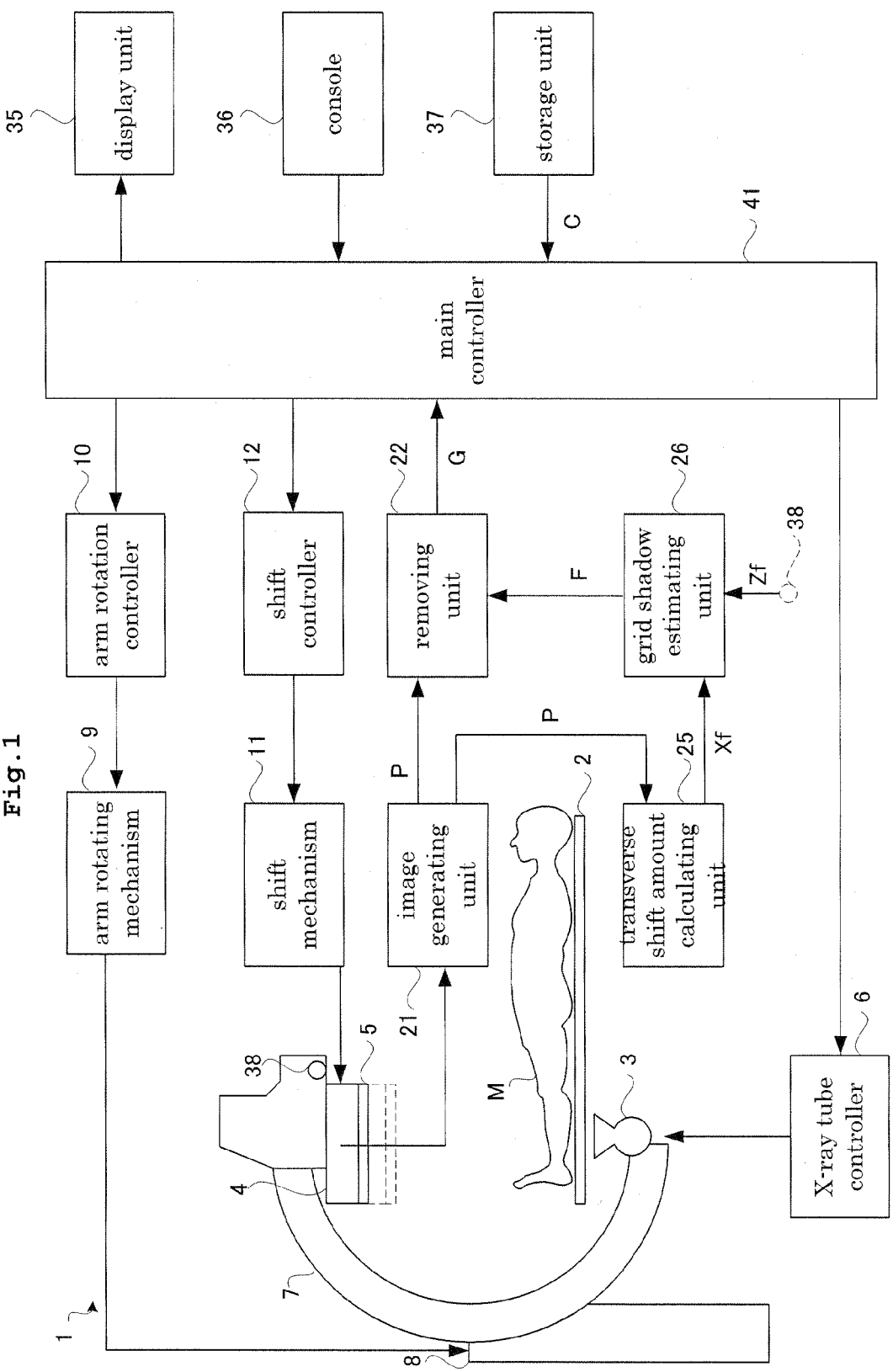
FIG. 1 is a functional block diagram illustrating a construction of an X-ray apparatus according to Embodiment 1.

A construction of an X-ray apparatus 1 in Embodiment 1 will be described first. FIG. 1 is a functional block diagram illustrating a construction of an X-ray apparatus according to Embodiment 1. As shown in FIG. 1, the X-ray apparatus 1 in Embodiment 1 includes a top board 2 for supporting a patient M, an X-ray tube 3 disposed below the top board 2, a flat panel detector: FPD 4 disposed above the top board 2 for detecting X-rays, and an X-ray grid 5 provided to cover an X-ray receiving, detecting plane of the FPD 4. The FPD 4 has X-ray detecting elements arranged vertically and horizontally on the detecting plane, to form a two-dimensional matrix of the detecting elements. The X-ray tube 3 corresponds to the radiation source in this invention. The FPD 4 corresponds to the radiation detecting device in this invention. The X-ray grid 5 corresponds to the radiation grid in this invention.

An X-ray tube controller 6 is provided for controlling a tube current and tube voltage of the X-ray tube 3, and pulse width of X-ray beams.

A C-arm 7 supports the X-ray tube 3 and FPD 4 together. The C-arm 7 is shaped arcuate, with the X-ray tube 3 attached to one end of the arc, and the FPD 4 attached to the other end. An arm rotating mechanism 9 is provided for rotating the C-arm 7. Assuming a plane including the arc of the arcuate C-arm 7 to be a reference plane, the C-arm 7 is rotatable about a first central axis extending perpendicular to the reference plane and passing through the center of curvature of the C-arm 7, and rotatable also about a second central axis, along the floor of an examination room, included in the reference plane. Thus, the C-arm 7 has the two central axes, and the rotations about these axes are independent of each other. The C-arm 7 is rotated by the arm rotating mechanism 9. An arm rotation controller 10 controls the arm rotating mechanism 9. This C-arm 7 is supported by a strut 8 installed on the floor of an examination room.

The FPD 4 has a shift mechanism 11 for shifting the FPD 4 forward and backward relative to the X-ray tube 3. Thus, the shift mechanism 11 can move the FPD 4 toward and away from the X-ray tube 3. A shift controller 12 controls the shift mechanism 11. A position sensor 38 attached to an FPD support provided at one end of the C-arm 7 and supporting the FPD 4 measures to what extent the FPD 4 should be shifted from a certain reference position relative to the X-ray tube 3. A range of shifting of the FPD 4 relative to the X-ray tube 3 is Zf. When this has a positive value, the FPD 4 is moved away from the X-ray tube 3, and when it has a negative value, the FPD 4 is moved toward the X-ray tube 3. The direction of the shift range measured by the position sensor 38 is from the X-ray tube 3 to the FPD 4. The shift range Zf is a relative distance between the X-ray tube and a detection system based on a standard SID distance (SID 0). For example, the shift range Zf is at +140 mm when the FPD 4 and X-ray tube 3 are at a maximum distance, and at −110 mm when the FPD 4 and X-ray tube 3 are at a minimum distance.

An image generating unit 21 generates an original image P reflecting a fluoroscopic image of the patient, from detection signals outputted from the FPD 4. This original image P includes also shadows of the X-ray grid 5, but these are removed by a removing unit 22. The shadows of the X-ray grid 5 appearing on the original image P are the superimposed grid shadows in this invention. The image generating unit 21 corresponds to the image generating device in this invention. The removing unit 22 corresponds to the removing device in this invention.

Figure 2:
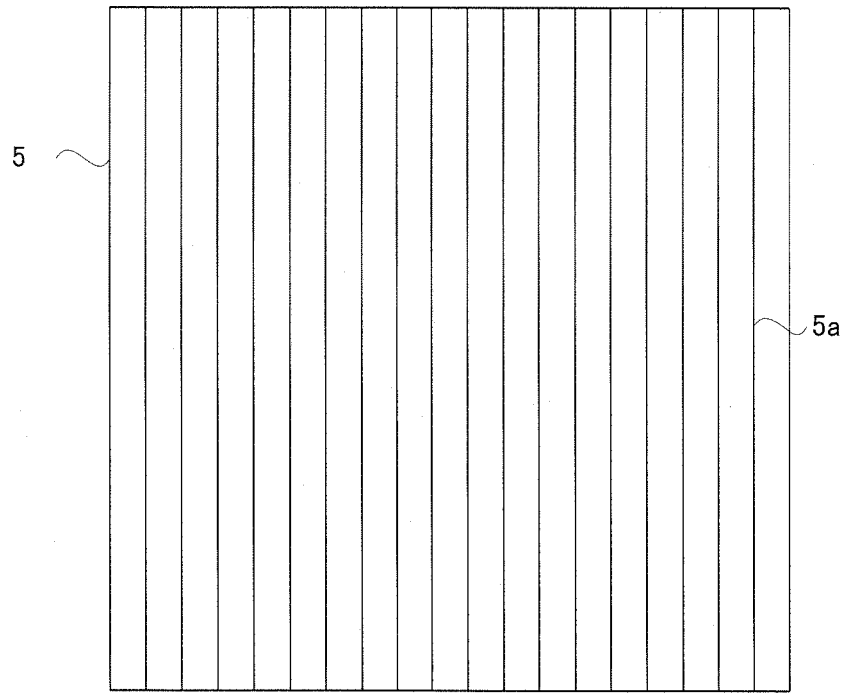
FIG. 2 is a schematic view illustrating shadows of an X-ray grid according to Embodiment 1.
Figure 3:
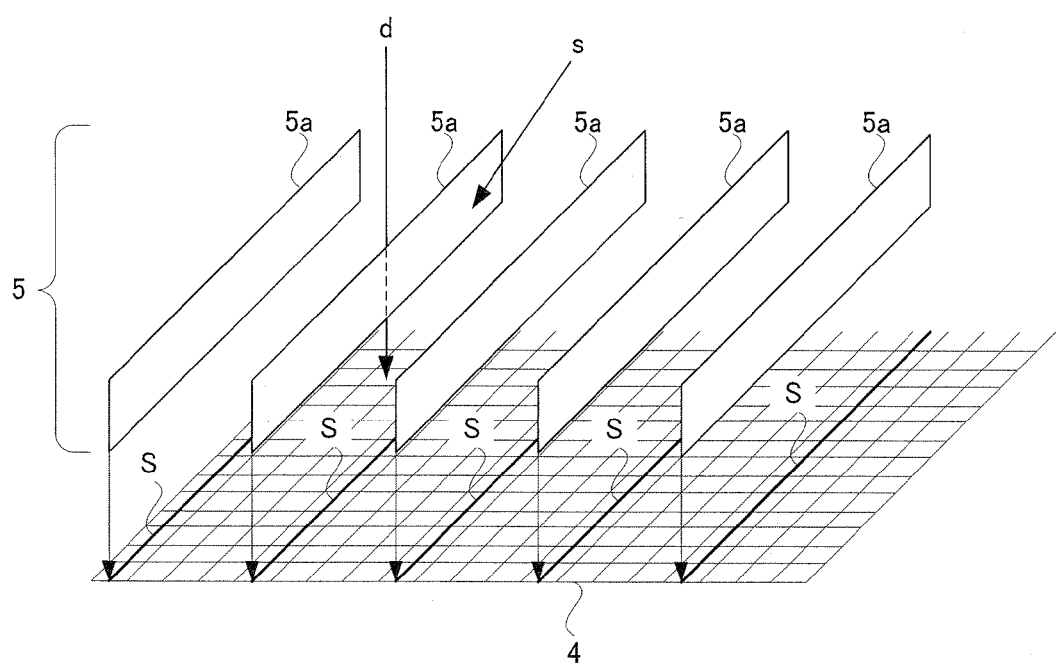
FIG. 3 is a schematic view illustrating a construction of the X-ray grid according to Embodiment 1.

The X-ray grid 5 is provided for removing scattered rays produced when X-rays are transmitted through the patient M. The X-ray grid 5 is a plate-like object which can cover the detecting plane, rectangular in shape, of the FPD 4, and includes absorbing foil strips 5*a* extending longitudinally (corresponding to the first direction in this invention) and arranged transversely (corresponding to the second direction in this invention) (see FIG. 2). The respective absorbing foil strips 5*a* are arranged to permit passage of direct X-rays d traveling linearly from the X-ray tube 3 to the FPD 4. Specifically, as shown in FIG. 3, the absorbing foil strips 5*a* are arranged to have the direction of width thereof in agreement with the traveling direction of the direct X-rays d. The X-ray grid 5 transmits only X-rays having the specific traveling direction. That is, the scattered rays having deflected traveling directions are absorbed by the X-ray grid 5, and do not reach the FPD 4.

The arrangement pitch in the transverse direction of the absorbing foil strips 5*a* is determined based on the arrangement pitch of the detecting elements of the FPD 4. The absorbing foil strips 5*a*, which have a certain thickness, block direct X-rays d though slightly. Shadows S of the absorbing foil strips 5*a* fall on the FPD 4 in an amount corresponding to the direct X-rays d blocked by the absorbing foil strips 5*a*. The absorbing foil strips 5*a* are positionally adjusted so that the shadows S of the absorbing foil strips 5*a* may appear in transversely middle positions of the detecting elements (see FIG. 3). The absorbing foil strips 5*a* are arranged in the transverse direction substantially four times the pitch in the transverse direction of the detecting elements. Since a cone-shaped X-ray beam is outputted from the X-ray tube 3, the shadows S of the X-ray grid 5 are enlarged when projected to the FPD 4. Since the arrangement pitch of the shadows S of the absorbing foil strips 5*a* is four times the arrangement pitch of the detecting elements, the pitch in the transverse direction of the absorbing foil strips 5*a* is made slightly less than four times the arrangement pitch in the transverse direction of the detecting elements.

Moreover, the arrangement pitch of the shadows S of the absorbing foil strips 5*a* is four times the arrangement pitch of the detecting elements as noted above, when the positional relationship between the FPD 4 and X-ray tube 3 is in the reference position. In practice, the FPD 4 moves forward and backward relative to the X-ray tube 3, and the FPD 4 and X-ray tube 3 may move in the direction of width of the X-ray grid 5. With variations in the relative position of the FPD 4 and X-ray tube 3, corresponding variations will take place in the positions of the shadows S of the absorbing foil strips 5*a* falling on the detecting plane of the FPD 4, and also in the arrangement pitch of the shadows S.

It is difficult to foresee how the shadows S will change with movement of the X-ray tube 3. It seems easy to determine movement of the shadows S geometrically if a range of movement of the X-ray tube 3 relative to the FPD 4 is known. However, this is limited to a case where the absorbing foil strips 5*a* are arranged in good order without being distorted. In actual cases, the absorbing foil strips 5*a* are gently bent, and are twisted as well. Therefore, complicated variations will occur with the shadows S as a result of movement of the X-ray tube 3.

Figure 4A:
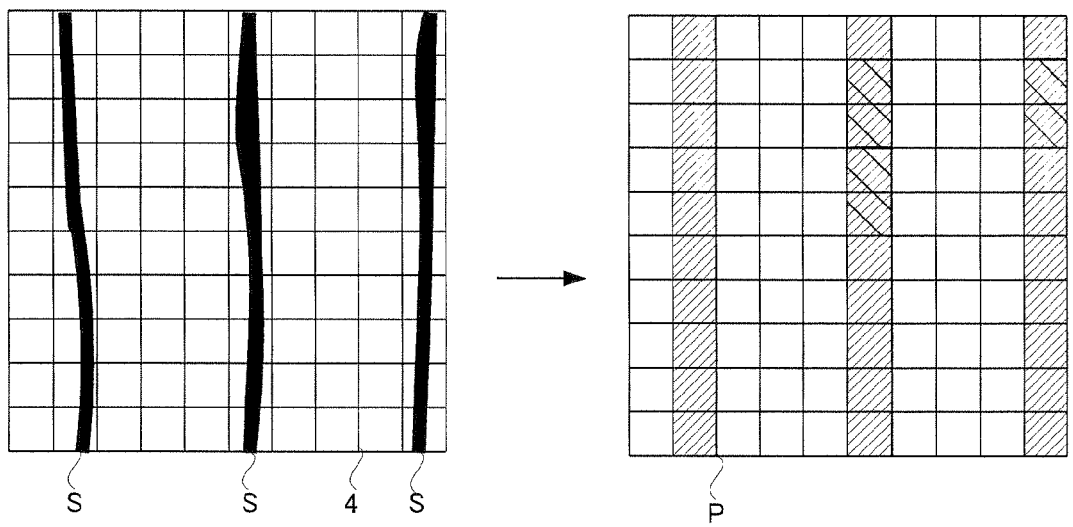
FIG. 4A is a schematic view illustrating a positional relationship between the X-ray grid and an FPD according to Embodiment 1.

Due to bending of the absorbing foil strips 5*a*, the shadows S falling on the FPD 4 are not linear, but are curved as shown in the left portion of FIG. 4A. The widths in the transverse direction of the shadows S falling on the FPD 4 are inconstant due to twisting of the absorbing foil strips 5*a*. When the FPD 4 detects radiation in the state shown in the left portion of FIG. 4A and an original image P is generated based thereon, dark striped pixels will appear as shown in the right portion of FIG. 4A. Since, in FIG. 4A, the shadows S are located in transversely middle positions of the detecting elements, the shadows S are arranged regularly in the original image P. However, since the widths of the shadows S are partially different, pixel values of the dark pixels are not constant.

Figure 4B:
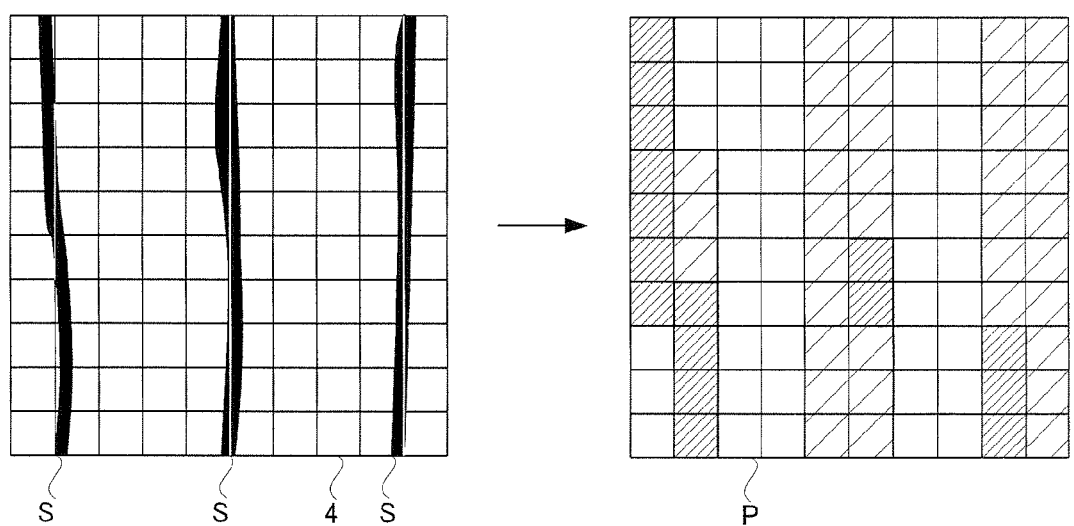
FIG. 4B is a schematic view illustrating the positional relationship between the X-ray grid and the FPD according to Embodiment 1.

FIG. 4B shows a case where the X-ray tube 3 has been shifted transversely relative to the FPD 4 from the state shown in FIG. 4A. The left portion of FIG. 4B shows the shadows S projected to the FPD 4, which are shifted leftward from the state shown in FIG. 4A. When the FPD 4 detects radiation in the state shown in the left portion of FIG. 4B and an original image P is generated based thereon, dark striped pixels will appear as shown in the right portion of FIG. 4B. Since, in FIG. 4B, the shadows S straddle transversely adjacent detecting elements, the shadows S are each distributed to two transversely adjacent detecting elements, and thus appear as having an increased width in the transverse direction on the original image P. Moreover, since the shadows S have curved shapes, the ratio in which the shadows S are distributed to the detecting elements varies with the vertical positions of the shadows S. Therefore, when the X-ray tube 3 moves relative to the FPD 4, the shadows of the X-ray grid 5 appearing on the original image P will vary in a complicated way.

The transverse movement of the X-ray tube 3 relative to the FPD 4 is caused by bending of the C-arm 7 under the weight of the X-ray tube 4 and FPD 4. The X-ray tube 3 is a heavy component, and the C-arm 7 will bend when rotated. This changes the positional relationship in the transverse direction between the FPD 4 and X-ray tube 3. As a specific example, a transverse shift amount within ±3 mm is conceivable.

Figure 5:
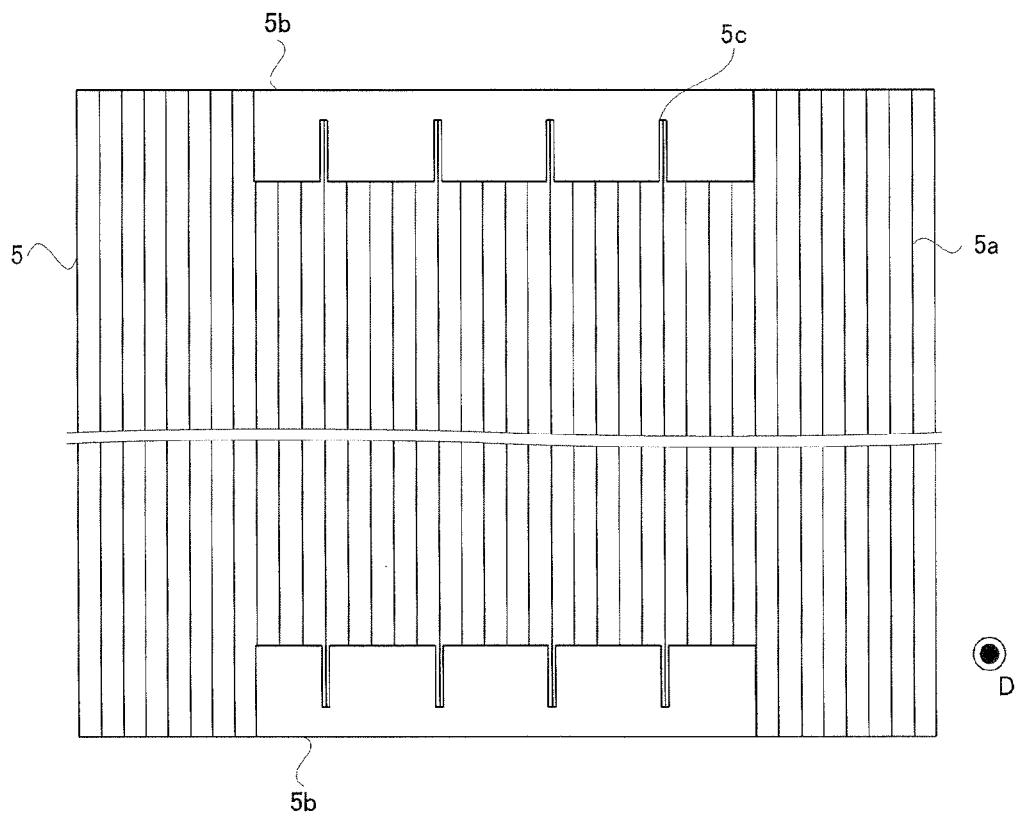
FIG. 5 is a plan view illustrating a construction of comb-like plates according to Embodiment 1.

Comb-like plates 5*b* provided for the purpose of calculating a transverse shift amount Xf (shift amount in the second direction) in real time will be described. As shown in FIG. 5, a pair of comb-like plates 5*b* are provided for the X-ray grid 5. The comb-like plates 5*b* are formed of a material that blocks off X-rays, and are strip-shaped members, whose longer direction corresponds to the transverse direction of the X-ray grid 5, and whose shorter direction corresponds to the longitudinal direction of the X-ray grid 5. The comb-like plates 5*b*, while being capable of serving the purpose, are small enough to present no obstacle to diagnostic imaging of the patient. These comb-like plates 5*b* are arranged at opposite ends in the longitudinal direction of the X-ray grid 5. The comb-like plates 5*b* are attached to the back surface (or may be the front surface) of the X-ray grid 5 as seen from the FPD 4. These comb-like plates 5*b* are provided for the purpose of detecting transverse shift amounts between the X-ray tube 3 and FPD 4. The comb-like plates 5*b* correspond to the shielding members in this invention. Direction D is a direction of thickness of the X-ray grid 5.

Each comb-like plate 5*b* has a plurality of grooves 5*c* extending in the longitudinal direction. When the surface of the X-ray grid 5 having the comb-like plates 5*b* are attached is seen, one of the absorbing foil strips 5a of the X-ray grid 5 is exposed from each groove 5c.

Figure 6:
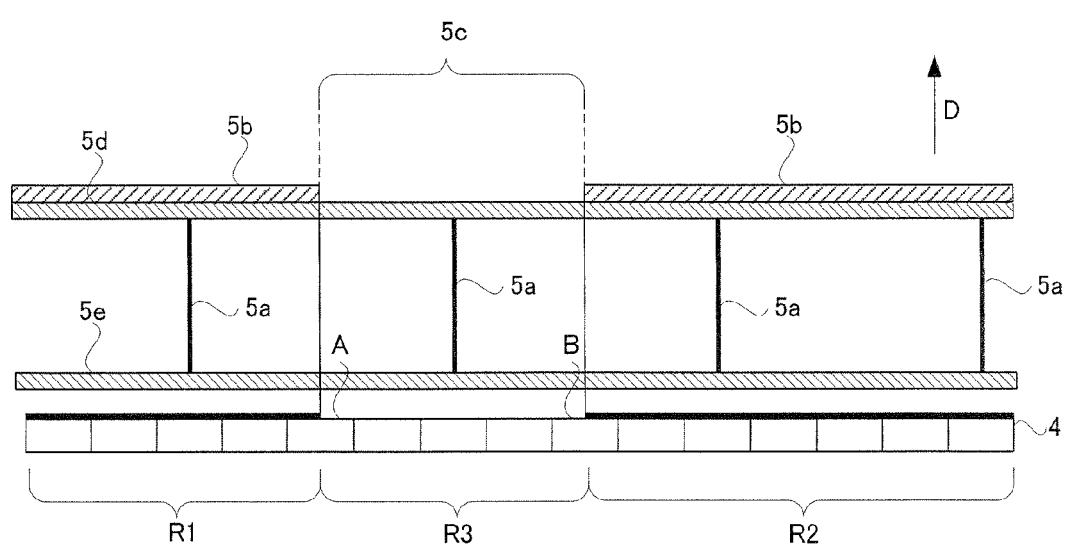
FIG. 6 is a schematic view illustrating a positional relationship between the comb-like plates and the FPD according to Embodiment 1.

FIG. 6 is a view of the X-ray grid 5 seen from a side thereof. Since the comb-like plates 5b attached absorb X-rays emitted, shadows of the comb-like plates 5b will fall on the FPD 4. In FIG. 6, areas R1 and areas R2 appearing on the detecting plane of the FPD 4 are the shadows of the comb-like plates 5b. Since the grooves 5c of the comb-like plates 5b allow passage of X-rays, the detecting plane of the FPD 4 will include areas R3 irradiated with X-rays and having a width in the transverse direction corresponding to that of the grooves 5c. The width in the transverse direction of the grooves 5c is determined based on the arrangement pitch in the transverse direction of the detecting elements of the FPD 4. Specifically, the width of the grooves 5c is substantially four times the arrangement pitch in the transverse direction of the detecting elements. That is, the width of the grooves 5c is substantially the same as the arrangement pitch of the absorbing foil strips 5a. The width of the grooves 5c may substantially be at least an integral multiple of the arrangement pitch of the absorbing foil strips 5a.

The members affixed with signs 5d and 5e in FIG. 6 are sheet-like grid covers combining the absorbing foil strips 5a into a unit. The grid covers have a property to transmit X-rays easily.

What is outputted from the X-ray tube 3 is a cone-shaped X-ray beam, and therefore the shadows of the comb-like plates 5b are enlarged when projected to the FPD 4. Since the width of areas R3 corresponds to four times the arrangement pitch of the detecting elements, the width of the grooves 5c becomes slightly less than the four times the arrangement pitch of the detecting elements.

A positional relationship between the X-ray grid 5 and comb-like plates 5b will be described. The comb-like plates 5b are positioned such that one end in the transverse direction of each area R3 coincides with a middle position in the transverse direction of a certain detecting element. The other end in the transverse direction of that area R3 also coincides with a middle position in the transverse direction of a different detecting element. The detecting elements having the ends of this area R3 are called a first detecting element A and a second detecting element B (see FIG. 6).

The first detecting element A and second detecting element B are in the positional relationship with the area R3 shown in FIG. 6 when the positional relationship between the FPD 4 and X-ray tube 3 corresponds to the reference position. When the relative position between the FPD 4 and X-ray tube 3 changes in the transverse direction, the position of the area R3 will change correspondingly.

Figure 7:
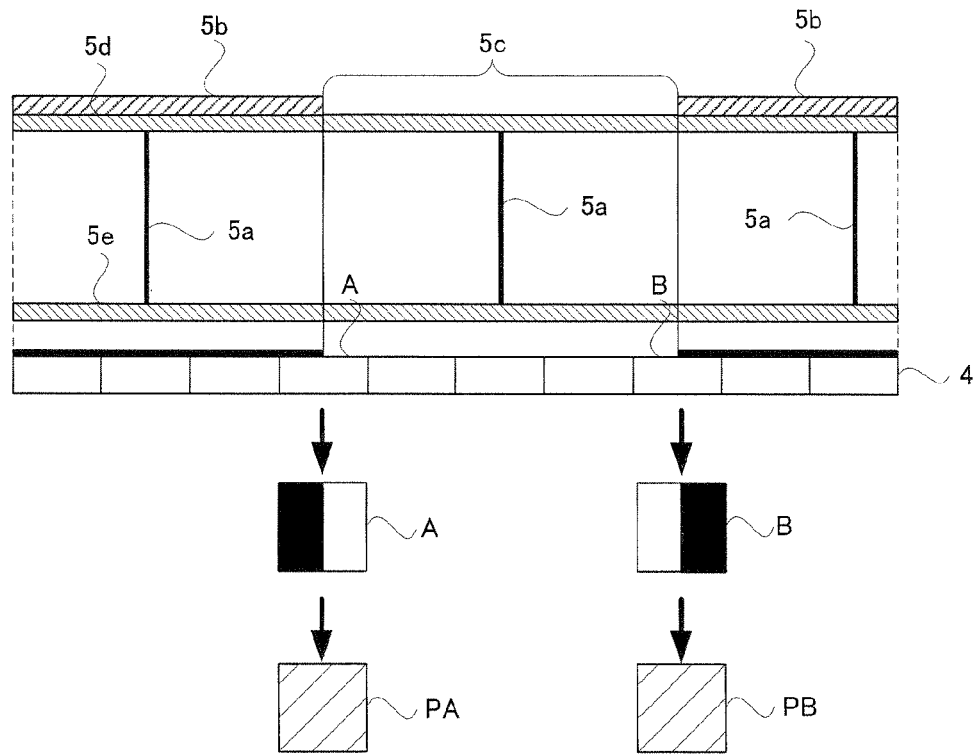
FIG. 7 is a schematic view illustrating the positional relationship between the comb-like plates and the FPD according to Embodiment 1.

FIG. 7 illustrates states of the detecting elements A and B when the positional relationship between the FPD 4 and X-ray tube 3 corresponds to the reference position. A shadow of the comb-like plate 5b falls on the left half of the first detecting element A, while X-rays having passed through the groove 5c are incident on the right half. Similarly, a shadow of the comb-like plate 5b falls on the right half of the second detecting element B, while X-rays having passed through the groove 5c are incident on the left half. When an original image P is acquired in this state, pixel PA corresponding to the first detecting element A and pixel PB corresponding to the second detecting element B will have the same pixel value.

Figure 8:
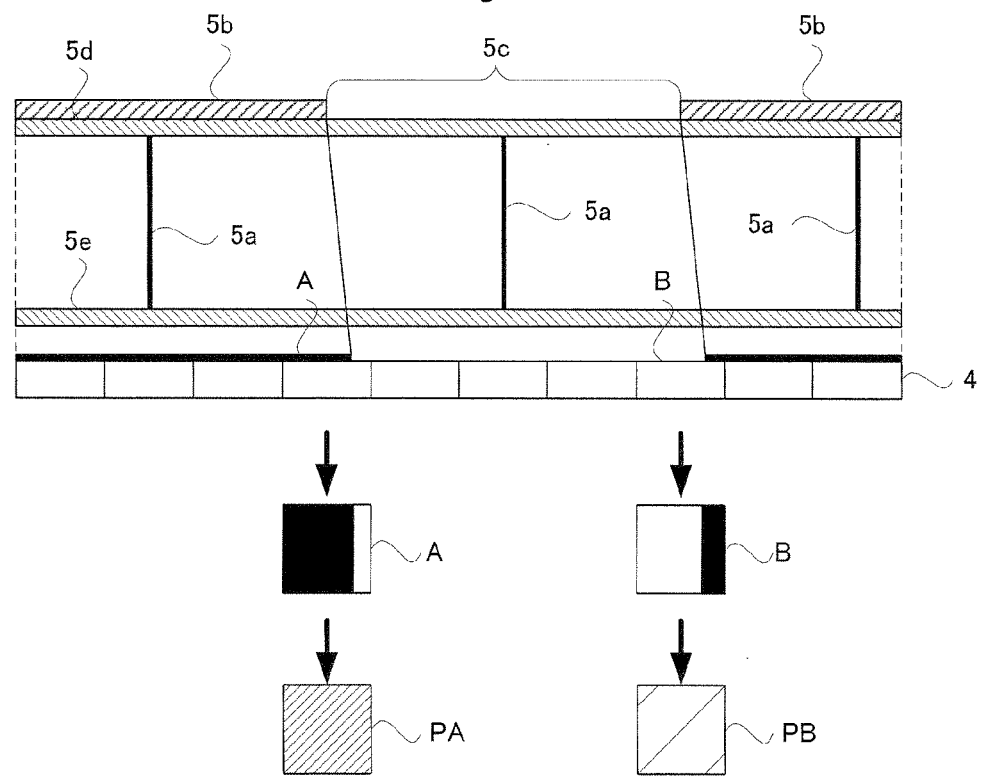
FIG. 8 is a schematic view illustrating the positional relationship between the comb-like plates and the FPD according to Embodiment 1.

FIG. 8 illustrates states of the detecting elements A and B when the positional relationship between the FPD 4 and X-ray tube 3 deviates from the reference position. A shadow of the comb-like plate 5b falls on a large part of the first detecting elements A. Similarly, X-rays having passed through the groove 5c are incident on a large part of the second detecting elements B. When an original image P is acquired in this state, pixel PA corresponding to the first detecting element A will become darker than what it is in FIG. 7, and pixel PB corresponding to the second detecting element B becomes brighter than what it is in FIG. 7. Thus, a transverse shift of the area R3 in FIG. 6 can be detected by obtaining pixel values of the pixels PA and PB in the original image P. While a projection image of the patient appears on the original image P, projection image values of the patient are substantially the same and can balance out, since the distance between the first detecting element A and second detecting element B is only 0.6 mm. It is thus possible to detect accurately a transverse shift amount Xf (shift amount in the second direction) of the X-ray tube 3 relative to the FPD 4. This transverse shift amount Xf is calculated by a transverse shift amount calculating unit 25. The transverse shift amount Xf corresponds to the second direction shift amount in this invention. The transverse shift amount calculating unit 25 corresponds to the transverse shift amount calculating device in this invention.

A grid shadow estimating unit 26 estimates a pattern of shadows of the X-ray grid 5 superimposed on the original image P based on the transverse shift amount Xf outputted from the transverse shift amount calculating unit 25 and the shift range Zf outputted from the position sensor 38. The pattern of shadows estimated by the grid shadow estimating unit 26 is an estimated grid shadow image F. The removing unit 22 removes the pattern of shadows of the X-ray grid 5 superimposed on the original image P, using the estimated shadow pattern image, and outputs a finished image G. The grid shadow estimating unit 26 corresponds to the grid shadow estimating device in this invention.

The X-ray apparatus 1 according to Embodiment 1 includes a main controller 41 for performing overall control of the controllers 6, 10 and 12. This main controller 41 has a CPU, and realizes the controllers 6, 10 and 12 and the components 21, 22, 25 and 26 relating to image generation, by executing various programs. Each component may be separate from the other to be operable by a corresponding control device. A display unit 35 is provided to display the finished image G, and a console 36 is provided to input controls by the operator.

A storage unit 37 stores all of preset values, reference data and outputs of the respective controllers 6, 10 and 12 and the respective components 21, 22, 25 and 26 relating to image generation. The storage unit 37 stores, for example, air radiographic images C described hereinafter. The storage unit 37 corresponds to the pattern storage device in this invention.

Figure 9:
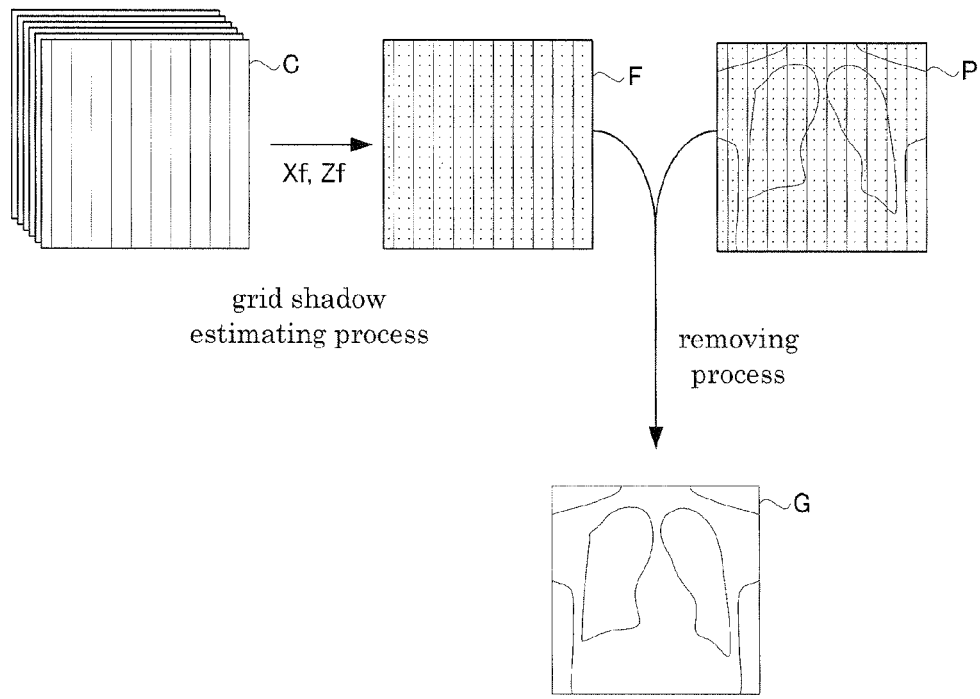
FIG. 9 is a schematic view illustrating a flow of image processing according to Embodiment 1.

The air radiographic images C will be described. The air radiographic images C are X-ray images of the X-ray grid 5 provided for the FPD 4, and seventy-two air radiographic images C are stored in the storage unit 37. As shown in FIG. 9, the air radiographic images C form the basis for the estimated grid shadow image F. These air radiographic images C are acquired as follows.

Figure 10:
FIG. 10 is a schematic view illustrating a method of acquiring air radiographic images according to Embodiment 1.

FIG. 10 is a view illustrating a method of acquiring the air radiographic images C. The air radiographic images C are acquired with the FPD 4 detached from the C-arm 7. That is, the air radiographic images are acquired in order to record a positional relationship of the grid 5 relative to the FPD 4 and distortion individuality of the absorbing foil strips 5a. It is therefore desirable to carry out air radiography on the delivery inspection bench at the factory as the final stage of manufacturing the X-ray tube 3 and FPD 4. A basic assumption is made that the X-ray tube 3 and FPD 4 are attached to the C-arm 7 in a hospital while the positional relationship of the grid 5 relative to the FPD 4 is maintained unchanged. The comb-like plates 5b are also attached to the grid 5, and the transverse shift amount Xf (shift amount in the second direction) is also acquired at the time of air radiography, which is compared with the transverse shift amount Xf outputted from the transverse shift amount calculating unit 25 at the time of original image collection with the X-ray tube 3 and FPD 4 attached to the C-arm 7 in the hospital. The air radiographic images C are acquired by emitting X-rays toward the FPD 4 having the X-ray grid 5 attached thereto. Air radiography means radiography carried out with no patient placed between the FPD 4 and X-ray source.

The X-ray tube 3 which emits X-rays is placed on a stage slidable transversely of the X-ray grid 5. Thus, the X-ray tube 3 can slide transversely from the reference position relative to the FPD 4.

The X-ray tube 3 slides transversely, stops, and emits X-rays to acquire an air radiographic image C. The moving pitch of the X-ray tube 3 is about 0.5 mm. This operation is repeated to acquire the air radiographic images C. A position in the transverse direction of the X-ray tube 3 at the time of radiography is related with each of the air radiographic images C. With movement of the X-ray tube 3, slightly varied patterns of the shadows of the X-ray grid 5 appear on the air radiographic images C. These air radiographic images C are stored in the storage unit 37.

Figure 11:
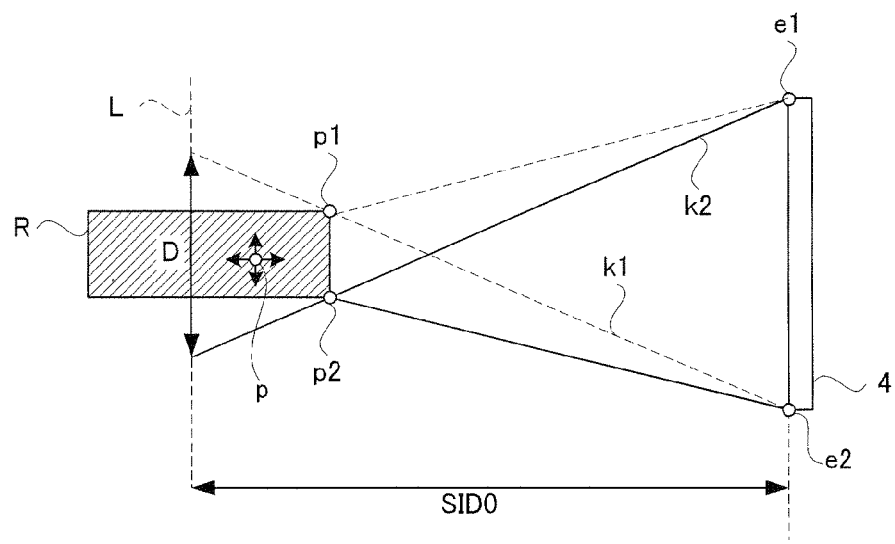
FIG. 11 is a schematic view illustrating a method of acquiring and calculating an estimated grid shadow image according to Embodiment 1.

This moving distance is determined as follows. FIG. 11 shows a state of the X-ray tube 3 and FPD 4 actually mounted on the C-arm 7. The X-ray tube 3 has a focus p movable toward and away from the FPD 4, and thus movable right and left on the plane of FIG. 11. The focus p is also shiftable in the second direction (up and down on the plane of FIG. 11) relative to the FPD 4. Therefore, the focus p will be located in any position inside a radiographic focal area R relative to the FPD 4 mounted on the C-arm 7 at the time of radiography. A specific example of the size of the area R is 250 mm in the right and left direction, which corresponds to the shift range (Zf), and 6 mm in the up-and-down direction at the time of scanning action of the C-arm 7.

Consider positions p1 and p2 where the focus p is at the least distance to the FPD 4 and shifted to a maximum extent in the second direction. Position p1 is at an upper right vertex of the rectangular area R. Position p2 is at a lower right vertex of the rectangular area R.

The X-ray beam emitted when the focus p is in position p1 diverges in the shape of a cone to fall on the FPD 4 between one end e1 and the other end e2 in the second direction (shown in dotted lines in FIG. 11). Attention is drawn to a straight line k1 extending at this time between position p1 located at one end and end e2 which is the other end in the second direction. When the focus p moves backward, and when the focus p moves toward position p2, the inclination of the straight line k1 becomes gentler and closer to the horizontal.

On the other hand, the X-ray beam emitted when the focus p is in position p2 diverges in the shape of a cone to fall on the FPD 4 between one end e1 and the other end e2 in the second direction (shown in solid lines in FIG. 11). Attention is drawn to a straight line k2 extending at this time between position p2 located at one end and end e1 located at the other end in the second direction. When the focus p moves backward, and when the focus p moves toward position p1, the inclination of the straight line k2 becomes gentler and closer to the horizontal.

When the focus p of the X-ray tube 3 is in any position inside the area R, the X-ray leaning most downward on the plane of FIG. 11, among the X-rays incident on the FPD 4, is an X-ray traveling along the straight line k1 and falling at the end e2 of the FPD 4, and the X-ray leaning most upward on the plane of FIG. 11, among the X-rays incident on the FPD 4, is an X-ray traveling along the straight line k2 and falling at the end e1 of the FPD 4. It is necessary to carry out radiography for acquiring the air radiographic images C in a way to include the X-rays having the most extreme direction.

Grid shadows appearing on the original image P can be estimated appropriately when the X-ray tube 3 on the slide stage moves relative to the FPD 4 as follows. When, for example, radiography is carried out to acquire air radiographic images C with the X-ray tube 3 and FPD 4 in the mutually closest state, the air radiographic images C may be acquired while moving the X-ray tube 3 to shift at intervals of 6 mm from position p1 to position p2. When, for example, the focus p of the X-ray tube 3 is at a distance of SID0 to the FPD 4, seventy-two air radiographic images C may be acquired while moving the focus p at intervals of 0.5 mm in a range of 36 mm from a position of intersection of a straight line L parallel to the FPD 4 and the straight line k1 to a position of intersection of the straight line L and the straight line k2.

An actual situation of image processing using the air radiographic images C will be described. As shown in FIG. 9, the grid shadow estimating unit 26 generates the estimated grid shadow image F based on the air radiographic images C stored in the storage unit 37. At this time, the transverse shift amount Xf and shift range Zf are taken into consideration. The removing unit 22 removes the shadows of the X-ray grid from the original image P using the estimated grid shadow image F.

Figure 12:
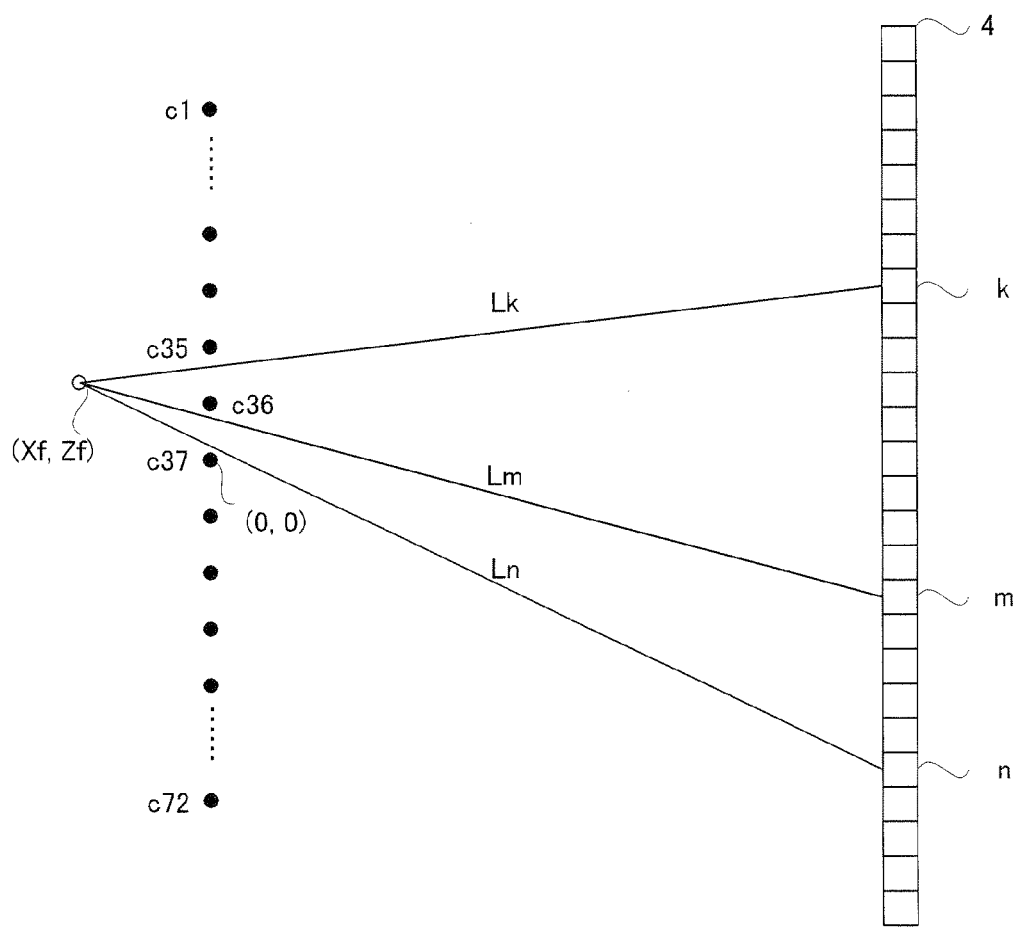
FIG. 12 is a schematic view illustrating the method of acquiring and calculating the estimated grid shadow image according to Embodiment 1.

Operation of the grid shadow estimating unit 26 for generating the estimated grid shadow image F will be described. The grid shadow estimating unit 26 estimates intensity of the shadows of X-ray grid 5 for all the detecting elements of FPD 4 using the air radiographic images C. This estimating method will be described. FIG. 12 is a schematic view illustrating operation of the grid shadow estimating unit 26. Point c1 in FIG. 12 signifies the position of the focus (position of an air focus) of the X-ray tube 3 when an air radiographic image C1 is acquired. That is, there are seventy-two air radiographic images C with different positions of the X-ray tube 3, and thus there are seventy-two air focuses c1-c72 corresponding to the air radiographic images C.

The focal position when the X-ray tube 3 is in the reference position is regarded as the origin (0, 0). It is assumed that the grid shadow estimating unit 26 estimates shadows of the X-ray grid 5 occurring when the focus of the X-ray tube 3 is at a point (Xf, Zf) spaced from the origin.

It is assumed that the grid shadow estimating unit 26 estimates a shadow of the X-ray grid 5 on a detecting element k in FIG. 12. The grid shadow estimating unit 26 derives a line segment Lk extending between the point (Xf, Zf) and detecting element k. The two air focuses close to this line segment Lk are c35 and c36. The grid shadow estimating unit 26 acquires air radiographic images C35 and C36 from the storage unit 37.

Figure 13:
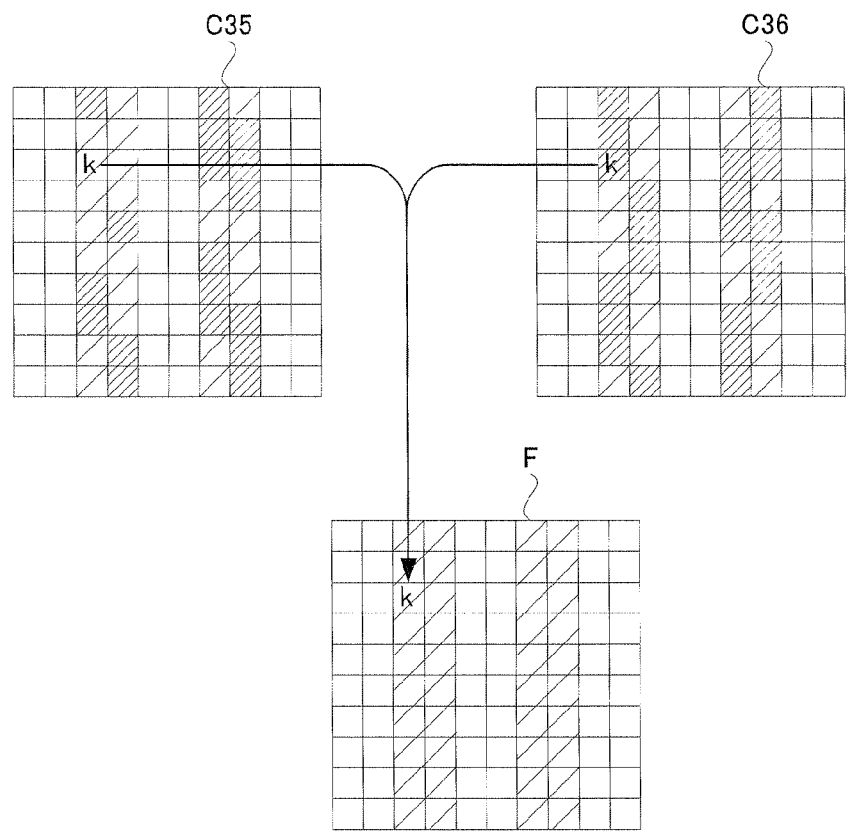
FIG. 13 is a schematic view illustrating the method of acquiring and calculating the estimated grid shadow image according to Embodiment 1.

Then, as shown in FIG. 13, the grid shadow estimating unit 26 reads pixel values of the pixels, corresponding to the detecting element k, in the air radiographic images C35 and C36, and generates a portion, corresponding to the detecting element k, of the estimated grid shadow image F by interpolation using these pixel values. The grid shadow estimating unit 26 carries out such operation for all the detecting elements, selecting two optimal air radiographic images C for interpolation each time.

Air radiographic images C referred to for estimation relating to detecting elements m and n in FIG. 12 are the same images C36 and C37. However, line segment Lm relating to the detecting element m is closer to point c36 than is line segment Ln relating to the detecting element n. It is imagined, therefore, that an interpolated value for the detecting element m on the estimated grid shadow image F is more influenced by the air radiographic image C36 than that for the detecting element n. In view of such a situation, the grid shadow estimating unit 26 is arranged to determine an interpolated value while linearly weighting two air radiographic images C based on a positional relationship between a line segment and two air focuses adjacent thereto. The estimated grid shadow image F is generated through such linear interpolating operations.

<Operation of the X-Ray Apparatus>

Next, operation of the X-ray apparatus 1 having the above construction will be described. To acquire an X-ray fluoroscopic image with the X-ray apparatus 1, the patient is first placed on the top board 2. The operator operates the console 36 to move the FPD 4 toward or away from the X-ray tube 3. The position sensor 38 measures a moving distance of the FPD 4, and outputs a shift range Zf to the grid shadow estimating unit 26.

When the operator instructs X-raying through the console 36, X-rays are emitted from the X-ray tube 3 toward the patient. X-rays transmitted through the patient and X-ray grid 5 reach the FPD 4. The FPD 4 outputs X-ray detection signals to the image generating unit 21. As shown in FIG. 9, the original image P generated by the image generating unit 21 has shadows of the X-ray grid 5 superimposed on a projection image of the patient. The original image P is outputted to the transverse shift amount calculating unit 25 and removing unit 22.

The shadows of the X-ray grid 5 appearing on the original image P vary with inclination of the C-arm 7. This is because bending of the C-arm 7 varies with the angle of inclination of the C-arm 7, and the transverse shift amount Xf of the X-ray tube 3 relative to the FPD 4 varies in response thereto. This transverse shift amount Xf is acquired by the transverse shift amount calculating unit 25, and is outputted to the grid shadow estimating unit 26. The grid shadow estimating unit 26 generates the estimated grid shadow image F using the shift range Zf, transverse shift amount Xf and air radiographic images C. The shift range Zf is acquired from the position sensor 38.

Figure 14:
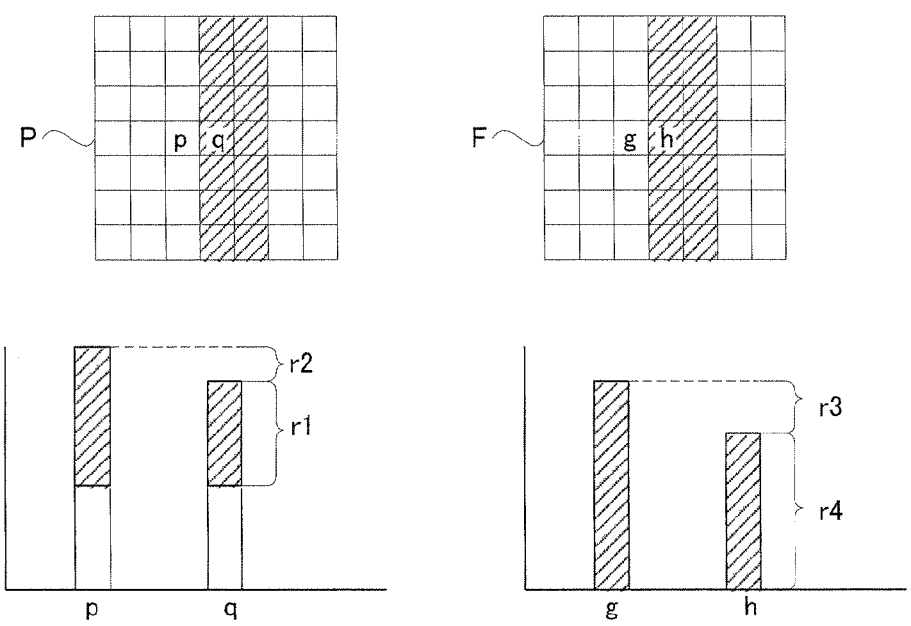
FIG. 14 is a schematic view illustrating operation of a removing unit according to Embodiment 1.

The original image P includes, besides the projection image of the patient and the shadows of the X-ray grid 5, scattered X-ray components not removed by the X-ray grid 5. First, the removing unit 22 removes these scattered X-ray components using the estimated grid shadow image F. The principle of removing the scattered X-ray components is as follows. The original image P in FIG. 14 includes two transversely adjacent pixels p and q. Pixel p is free of the shadows of the X-ray grid 5, but pixel q has a shadow appearing thereon. The pixel value of pixel p is higher than the pixel value of pixel q. As shown in the lower left portion of FIG. 14, the breakdown is a sum of direct X-ray components shown with slashes and scattered X-ray components shown without slashes. The scattered X-ray components do not significantly vary among different positions on the original image P, and can be regarded as being in the same quantity for pixels p and q. The quantity of direct ray components r1 for pixel q should be substantially the same as that for pixel p, but in practice, pixel q is darker by r2 in FIG. 14 under the influence of the shadow of an absorbing foil strip 5a.

On the other hand, the estimated grid shadow image F also includes two transversely adjacent pixels g and h. The position of pixel p in the original image P corresponds to the position of pixel g in the estimated grid shadow image F. The position of pixel q in original image P corresponds to the position of pixel h in the estimated grid shadow image F.

The pixel value of pixel g is higher than the pixel value of pixel h. As shown in the lower right portion of FIG. 14, the breakdown is direct X-ray components shown with slashes. Since the air radiographic images C are acquired without the patient in place, scattered X-ray components are not included in the estimated grid shadow image F. The quantity of direct ray components r4 for pixel h should be substantially the same as that for pixel g, but in practice, pixel h is darker by r3 in FIG. 14 under the influence of the shadow of an absorbing foil strip 5a.

Here, a relation of $r2/(r1+r2)=r4/(r3+r4)$ is formed. Therefore, if r2, r3 and r4 are known, r1 will be known. r1 represents the direct X-ray components for pixel q. Since the pixel value of pixel q is a sum of the direct X-ray components and scattered X-ray components, the scattered X-ray components for pixel q can be determined by subtracting the direct X-ray components from the pixel value of pixel q. The scattered X-ray components of pixel p are substantially the same as those of pixel q. The removing unit 22 removes the scattered X-ray components from the original image P based on such principle, using r2, r3 and r4.

The removing unit 22 removes the shadows of the X-ray grid 5 from the original image P by dividing the original image P after the scattered X-ray component removal by the estimated grid shadow image F. The finished image G generated in this way is displayed on the display unit 35, to complete the operation of the X-ray apparatus 1.

As described above, the X-ray apparatus 1 according to Embodiment 1 can remove from the original image P the shadows of the X-ray grid 5 appearing on the original image P. It is difficult to foresee the shape of the shadows of the X-ray grid 5 appearing on the original image P. This is because the mechanical construction of the X-ray grid 5 does not conform to the setting. Moreover, the shape of the shadows of the X-ray grid 5 appearing on the original image P varies with the positional relationship between the X-ray tube 3 and FPD 4, which makes it still more difficult to foresee the shape of the shadows of the X-ray grid 5 appearing on the original image P. The construction of Embodiment 1 includes the grid shadow estimating unit 26 which estimates a pattern of the shadows of the X-ray grid 5 appearing on the original image P from a plurality of patterns of the shadows stored in the storage unit 37, and the removing unit 22 which removes the shadows of the X-ray grid 5 from the original image P based on the estimated shadows of the X-ray grid 5 appearing on the original image P. The grid shadow estimating unit 26 estimates the shadows of the X-ray grid 5 appearing on the original image P based on the positional relationship between the X-ray tube 3 and FPD 4 occurring at the time of acquiring the original image P. Therefore, the construction of Embodiment 1 can remove from the original image P the shadows of the X-ray grid 5 appearing on the original image P.

According to the construction of Embodiment 1, the shadows of the X-ray grid 5 appearing on the original image P are estimated using the transverse shift amount Xf of the X-ray tube 3 and FPD 4 in the direction of arrangement of the absorbing foil strips 5a (in the second direction). When the X-ray tube 3 shifts in the transverse direction relative to the FPD 4, the shape of the shadows of the X-ray grid 5 appearing on the original image P will change significantly. In view of such a situation, the above construction takes the transverse shift amount Xf into consideration in estimating the shape of the shadows of the X-ray grid 5 appearing on the original image P.

According to the above construction, the range of movement of the X-ray tube 3 at the time of radiographing the patterns of the shadows of the X-ray grid 5 is determined with reference to the state where the X-ray tube 3 and FPD 4 are the closest to each other when acquiring the original image P of the patient. In this state, as seen from the FPD 4, an apparent moving range in the second direction of the X-ray tube 3 becomes the most intense. According to the above construction, even when the X-ray tube 3 and FPD 4 are the closest to each other, a pattern of the shadows of the X-ray grid 5 can be acquired reliably. Consequently, the storage unit 37 can exhaustively store data about possible shapes of the superimposed grid shadows.

The construction in Embodiment 1 calculates the transverse shift amount Xf specifically as follows. The X-ray grid 5 has, attached thereto, the comb-like plates 5b having grooves 5c extending in the longitudinal direction. The transverse shift amount Xf at the time of acquiring the original image P is calculated based on the shadows of the comb-like plates 5b appearing on the original image P. Consequently, the transverse shift amount Xf is calculated reliably.

With the pair of comb-like plates 5b provided at the opposite ends in the longitudinal direction of the X-ray grid 5, the transverse shift amount Xf can be calculated for two locations on the X-ray grid 5. Thus, the transverse shift amount Xf is calculated reliably.

The air radiographic images C stored in the storage unit 37 are radiological images which have, related thereto, position information on the X-ray tube 3 relative to the FPD 4 at times the radiological images are acquired. The position information related with the radiological images is referred to when estimating the pattern of shadows of the X-ray grid 5 appearing on the original image P.

The pattern of shadows of the X-ray grid 5 appearing on the original image P is estimated using linear interpolation. In this way, the shadows of the X-ray grid 5 appearing on the original image P can be estimated more simply.

The above construction provides the shift mechanism 11 for moving the FPD 4 toward and away from the X-ray tube 3. This varies the distance between the FPD 4 and X-ray tube 3. Even so, the X-ray apparatus 1 according to the construction in Embodiment 1 estimates the pattern of shadows of the X-ray grid 5 appearing on the original image P according to the positional relationship between the FPD 4 and X-ray tube 3. Thus, the shadows of the X-ray grid 5 can be removed reliably from the original image P.

This invention is not limited to the foregoing construction, but may be modified as follows:

(1) The following modification is possible from a viewpoint of when to calculate the estimated grid shadow image F. The storage unit 37 described above stores the air radiographic images C, and the grid shadow estimating unit 26 generates the estimated grid shadow image F using the air radiographic images C. In place of such arrangement, estimated grid shadow images F may be stored beforehand in the storage unit 37. The storage unit 37 stores a plurality of estimated grid shadow images F related with corresponding transverse shift amounts Xf and shift ranges Zf. The grid shadow estimating unit 26 may fetch from the storage unit 37 an estimated grid shadow image F corresponding to the transverse shift amount Xf and shift range Zf outputted from the transverse shift amount calculating unit 25 and grid shadow estimating unit 26, and output this estimated grid shadow image F to the removing unit 22. This can significantly reduce the burden of calculation on the grid shadow estimating unit 26.

The following construction is conceivable for such a modification. In advance of original image radiography, the grid shadow estimating unit 26 calculates and acquires patterns of shadows of the X-ray grid 5 discretely while virtually changing the positional relationship between the X-ray tube 3 and FPD 4 within an assumable range, and stores the patterns of shadows in the storage unit 37. When an actual original image PO is acquired, the removing unit 22 determines positional relationships between the X-ray tube 3 and FPD 4 by referring to shift ranges Zf and transverse shift amounts Xf outputted successively, and removes the shadows of the X-ray grid 5 from the original image using the pattern of shadows of the X-ray grid 5 acquired from the nearest positional relationship.

To make the above method simpler, based on a shift range Zf set in advance of original image radiography, the grid shadow estimating unit 26 may calculate and acquire patterns of shadows of the X-ray grid 5 discretely while virtually changing the transverse shift amount Xf between the X-ray tube 3 and FPD 4, and store the patterns of shadows in the storage unit 37. The removing unit 22 removes the shadows of the X-ray grid 5 from the original image using the pattern of shadows of the X-ray grid 5 acquired from the positional relationship nearest to the transverse shift amount Xf at the time of original image radiography. Such construction is effective when the shift range Zf remains faithful to the setting during radiography of the original image P.

The above construction is suitable where original image radiography is carried out a plurality of times with high frequency, such as dynamic image radiography or tomography. That is, the patterns of shadows of the X-ray grid 5 are acquired beforehand by the grid shadow estimating unit 26, and there is no need to estimate a pattern of shadows of the X-ray grid 5 when the original image is acquired. The removing unit 22 removes the shadows of the X-ray grid 5 from the original image using the pattern of shadows of the X-ray grid 5 acquired from a positional relationship nearest to the positional relationship between the X-ray tube 3 and FPD 4 at the time of original image radiography. Thus, when the radiography is completed, the pattern of superposed grid shadows can be removed promptly.

The construction may be modified such that, based on a shift range Zf set in advance of original image radiography, the grid shadow estimating unit 26 calculates and acquires patterns of shadows of the X-ray grid 5 discretely while virtually changing the transverse shift amount Xf between the X-ray tube 3 and FPD 4. Such modification can simplify operation of the grid shadow estimating unit 26.

Figure 15:
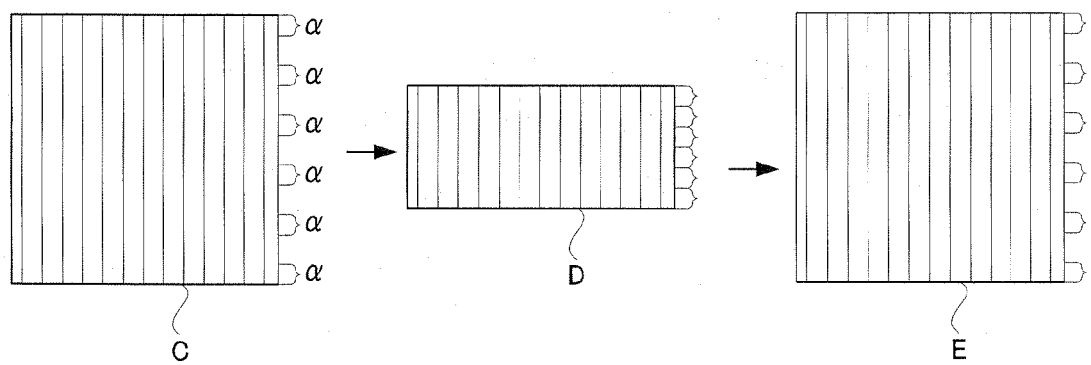
FIG. 15 is a schematic view illustrating a construction according to a modification of this invention.

(2) In this invention, the air radiographic images C can be stored as compressed in the longitudinal direction. The air radiographic images C are images with little variation in the longitudinal direction. Thus, as shown in FIG. 15, each air radiographic image C may be thinned out in the longitudinal direction to be stored as compressed image D in the storage unit 37. As a method of compressing the air radiographic image C, the compressed image D may be generated by connecting belt-like areas a each having a width corresponding to one pixel in the longitudinal direction of the air radiographic image C. In the air radiographic image C, the belt-like areas a are separated by 10 pixels in the longitudinal direction. When importance is placed on the statistical accuracy of the image, the compressed image may be formed of data derived from an additive averaging (or weighted averaging) of rows of suitable width (e.g. an additive averaging of 32 rows carried out every 32 rows).

The grid shadow estimating unit 26 develops the compressed image D to generate a developed image E. As a specific method therefor, it is conceivable to generate the developed image E by linearly interpolating areas between the belt-like areas α in the compressed image D.

Figure 16:
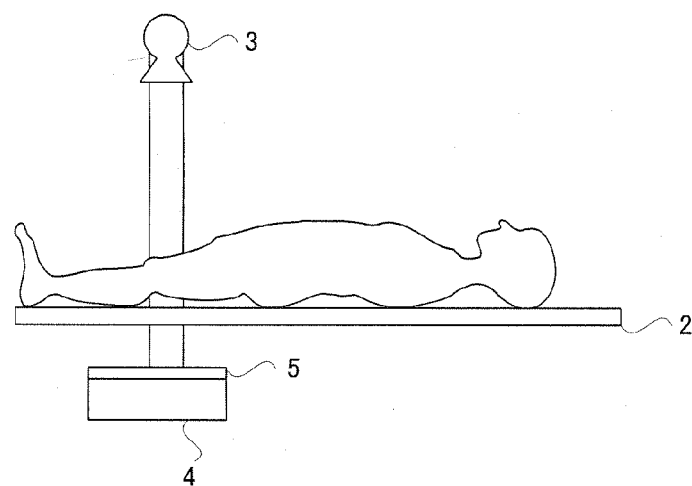
FIG. 16 is a schematic view illustrating a construction according to a modification of this invention.

(3) The construction in Embodiment 1 provides a C-arm. Instead, as shown in FIG. 16, the invention may be applied to a radiographic apparatus of the type having the X-ray tube 3 supported by a strut (commonly known as fluoroscopic table).

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus for acquiring fluoroscopic images of an object under examination, comprising:
   a radiation source for emitting radiation;
   a radiation detecting device for detecting the radiation;
   a radiation grid placed to cover a radiation detecting plane of the radiation detecting device;
   a pattern storage device for storing a plurality of patterns of shadows of the radiation grid falling on the radiation detecting device;
   an image generating device for generating an original image showing the object under examination and the shadows of the radiation grid, based on detection signals outputted from the radiation detecting device;
   a grid shadow estimating device for estimating a pattern of superimposed grid shadows, which are the shadows of the radiation grid appearing on the original image, from the patterns of shadows stored in the pattern storage device; and
   a removing device for removing the shadows of the radiation grid from the original image based on the superimposed grid shadows estimated;
   wherein the grid shadow estimating device is arranged to estimate the superimposed grid shadows based on a positional relationship between the radiation source and the radiation detecting device occurring at a time of acquiring the original image.

2. The radiographic apparatus according to claim 1, wherein:
   the radiation grid includes absorbing foil strips extending in a first direction and arranged in a second direction;
   the grid shadow estimating device is arranged to estimate the superimposed grid shadows based on the positional relationship between the radiation source and the radiation detecting device occurring at the time of acquiring the original image, which relationship includes (A) a shift range which is a range of variations in a distance between the radiation source and the radiation detecting device, and (B) a second direction shift amount which is an amount of shift in the second direction between the radiation source and the radiation detecting device; and
   the patterns of shadows of the radiation grid stored in the pattern storage device are obtained by serially acquiring radiological images while moving the radiation source at predetermined intervals in the second direction relative to the radiation detecting device, with the radiation grid covering the detecting plane of the radiation detecting device.

3. The radiographic apparatus according to claim 2, wherein the intervals for moving the radiation source when obtaining the patterns of shadows of the radiation grid are determined to include:
   a radiation emitted from the radiation source toward one end in the second direction of the radiation detecting device when the radiation source and the radiation detecting device have a minimum distance therebetween at the time of acquiring the original image, and when the radiation source is shifted to a maximum extent toward the other end in the second direction; and
   a radiation emitted from the radiation source toward the other end in the second direction of the radiation detecting device when the radiation source and the radiation detecting device have the minimum distance therebetween at the time of acquiring the original image, and when the radiation source is shifted to a maximum extent toward the one end in the second direction.

4. The radiographic apparatus according to claim 2, wherein the patterns of shadows of the radiation grid stored in the pattern storage device are compressed in the first direction.

5. The radiographic apparatus according to claim 2, wherein the radiation grid includes shielding members attached thereto and having grooves extending in the first direction, the second direction being a longitudinal direction, and the first direction being a transverse direction,
   the apparatus further comprising a shift amount calculating device for calculating the second direction shift amount at the time of acquiring the original image, based on shadows of the shielding members appearing on the original image.

6. The radiographic apparatus according to claim 5, wherein the shielding members are provided as a pair which are arranged at opposite ends in the first direction of the radiation grid.

7. The radiographic apparatus according to claim 2, wherein:
   the patterns of shadows of the radiation grid stored in the pattern storage device are radiological images;
   the radiological images having, related therewith, position information on the radiation source relative to the radiation detecting device at times the radiological images are acquired; and
   the grid shadow estimating device is arranged to estimate the pattern of the superimposed grid shadows while referring to the position information related with the radiological images.

8. The radiographic apparatus according to claim 7, wherein the grid shadow estimating device is arranged to estimate the pattern of the superimposed grid shadows by linearly interpolating the radiological images in the second direction.

9. The radiographic apparatus according to claim 2, wherein:
   the grid shadow estimating device is arranged, in advance of original image radiography, to calculate and acquire the patterns of shadows of the radiation grid discretely while virtually changing the positional relationship between the radiation source and the radiation detecting device; and
   the removing device is arranged to remove the shadows of the radiation grid from the original image using a pattern of shadows of the radiation grid acquired from a positional relationship nearest to the positional relationship at the time of original image radiography.

10. The radiographic apparatus according to claim 9, wherein:
    the grid shadow estimating device is arranged, based on a shift range set in advance of original image radiography, to calculate and acquire the patterns of shadows of the radiation grid discretely while virtually changing the second direction shift amount between the radiation source and the radiation detecting device; and the removing device is arranged to remove the shadows of the radiation grid from the original image using a pattern of shadows of the radiation grid acquired from a positional relationship nearest to the positional relationship at the time of original image radiography.

* * * * *